United States Patent [19]

Baxter, Jr.

[11] Patent Number: 5,750,802
[45] Date of Patent: May 12, 1998

[54] (1R*, 2S)-1-PHENYL-2-NITROALCOHOLS AND METHOD FOR PRODUCING SAME

[75] Inventor: C. Edward Baxter, Jr., Fountain Valley, Calif.

[73] Assignee: Amvac Chemical Corporation, Los Angeles, Calif.

[21] Appl. No.: 904,242

[22] Filed: Jul. 31, 1997

Related U.S. Application Data

[63] Continuation of Ser. No. 472,343, Jun. 7, 1995, abandoned.

[51] Int. Cl.⁶ ........................ C07C 27/00
[52] U.S. Cl. ........................ 568/814; 568/705
[58] Field of Search ........................ 568/705, 814

[56] References Cited

U.S. PATENT DOCUMENTS

| | | |
|---|---|---|
| 1,356,877 | 10/1920 | Nagai . |
| 1,399,144 | 12/1921 | Nagai . |
| 1,973,647 | 9/1934 | Nagai . |
| 2,347,621 | 4/1944 | Tindall . |
| 3,028,429 | 4/1962 | Wilbert et al. . |
| 4,224,246 | 9/1980 | Hodge . |
| 4,416,827 | 11/1983 | Bethge et al. . |
| 5,099,067 | 3/1992 | Barrett et al. . |

OTHER PUBLICATIONS

Hartung et al., *Organic Synthesis*, vol. 2, 363–364, 1930.
Hartung et al., *J. Am. Chem. Soc.*, vol. 51, 2262–2266 (1929).
Hoover et al., *J. Org. Chem.*, vol. 12, 506–509 (1974).
Casreact 115:114070, Fernandez, RX(2), 1991.

*Primary Examiner*—Samuel Barts
*Attorney, Agent, or Firm*—Pillsbury Madison & Sutro LLP

[57] ABSTRACT

A 1-phenyl-2-nitroalcohol of the formula I

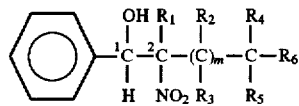

having a (1R*,2S*) stereoisomer and a (1R*2R*) stereoisomer is produced by reacting benzaldehyde with a nitroalkane in the presence of an amine catalyst. The resulting 1-phenyl-2-nitroalcohol includes at least 50% of the (1R*, 2S*) stereoisomer.

20 Claims, No Drawings

(1R*, 2S)-1-PHENYL-2-NITROALCOHOLS AND METHOD FOR PRODUCING SAME

This is a continuation of application Ser. No. 08/472,343 filed on Jun. 7, 1995, now abandoned.

FIELD OF THE INVENTION

The present invention relates to (1R*,2S*)-1-phenyl-2-nitroalcohols, specifically (1R*,2S*)-2-nitro-1-phenyl-1-propanol and its homologs and methods for their production.

BACKGROUND OF THE INVENTION

Phenylpropanolamine is a common component of many over-the-counter cough and cold formulations, as well as the active ingredient of many appetite suppressant products. Phenylpropanolamine, however, can exist as two separate compounds which are stereoisomers of each other, (1R*, 2S*)-phenylpropanolamine and (1R*,2R*)-phenylpropanolamine. The physical properties of the two stereoisomers are different. (1R*,2S*)-phenylpropanolamine, also called dl-norephedrine, is the desired stereoisomer and is the product specified by the United States Pharmacopeia XXII (USP). (1R*,2R*)-phenylpropanolamine, also called dl-isonorephedrine, will not meet the specifications of USP XXII. Phenylpropanolamine USP, therefore, is synonymous with (1R*,2S*)-phenylpropanolamine, or dl-norephedrine.

One method of currently manufacturing phenylpropanolamine is the reaction of propiophenone with an alkyl nitrite followed by catalytic reduction (hydrogenation) of the isonitrosopropiophenone intermediate. This process is described, for example, by Hartung and Crossley, *Organic Synthesis*, Vol. 2, pp. 363–364; Hartung and Munch, "Amino Alcohols. I. Phenylpropanolamine and Para-Tolylpropanolamine," *J. Am. Chem. Soc.*, Vol. 51, p. 2264 (1929); Wilbert et al., U.S. Pat. No. 3,028,429. The main advantage of this process is that it produces essentially 100% of the desired dl-norephedrine stereoisomer. Such process, however, has significant disadvantages. It is a multi-step process with only moderate yields at each step resulting in relatively low overall yields. In addition, the manufacturing process generates large quantities of hazardous waste, disposal of which is expensive.

Phenylpropanolamine can also be manufactured by the reaction of benzaldehyde with nitroethane followed by catalytic reduction of the intermediate nitro-alcohol, 2-nitro-1-phenyl-1-propanol. This process is described by Hoover et al., "Synthesis of 2-Amino-1-Phenyl-1-Propanol and Its Methylated Derivatives," *J. Org. Chem.*, Vol. 12, pp. 506–509 (1947), and has the advantage of almost no waste generation. The process, however, has a serious disadvantage in that the nitro-alcohol intermediate, itself, is produced as an stereoisomeric mixture of (1R*,2S*)-2-nitro-1-phenyl-1-propanol and (1R*,2R*)-2-nitro-1-phenyl-1-propanol having a low fraction of the desired (1R*,2S*)-2-nitro-1-phenyl-1-propanol stereoisomer. Upon reduction, the fraction of the desired phenylpropanolamine stereoisomer, dl-norephedrine, is only about 30–35%, the remaining amount being the other stereoisomer, dl-isonorephedrine. Attempts by these earlier workers to resolve the phenylpropanolamine stereoisomers in sufficient yields to be practical were unsuccessful and this process was abandoned in favor of the current propiophenone process.

U.S. Pat. Nos. 1,356,877 and 1,973,647, to Nagai, describing the benzaldehyde process for the production of ephedrine homologs, disclose the use of catalysts such as alkali metal carbonates, bicarbonates, phosphates, or pyridine. The use of alkali hydroxides in the reaction mixture is described by Vanderbilt and Hass, *Ind. Eng. Chemistry*, Vol. 32, p. 34 (1940). However, these methods have the same disadvantages described above, namely, that the reduction product contains only relatively small amounts of the desired stereoisomer, overall conversion is low and the reaction proceeds slowly.

Kamlet, U.S. Pat. No. 2,151,517, addressed the problem of low reactivity and conversion of the catalytic alkali carbonates and hydroxides by first making the alkali metal salt of the nitroalkane and reacting that with the bisulfite addition product of benzaldehyde. This process was successful in increasing the conversion of the reactants and significantly reducing the reaction time but still produced a nitro-alcohol product having a low fraction of the desired (1R*,2S*) stereoisomer.

A need exists for precursors of dl-norephedrine and its homologs. In particular, 1-phenyl-2-nitroalcohols with an increased fraction of the desired (1R*,2S*)-1-phenyl-2-nitroalcohol stereoisomer are needed. Upon reduction of (1R*,2S*)-1-phenyl-2-nitroalcohols, high yields of the desired (1R*,2S*)-phenylpropanolamine homologs would be produced.

A need also exists for an improved process for producing 1-phenyl-2-nitroalcohol precursors of dl-norephedrine and its homologs. This method should produce 1-phenyl-2-nitroalcohols having an increased fraction of the desired (1R*,2S*)-1-phenyl-2-nitroalcohol stereoisomer. The process should also produce the desired (1R*,2S*)-1-phenyl-2-nitroalcohol product with high overall reactant conversion and a short reaction time.

SUMMARY OF THE PREFERRED EMBODIMENTS

In accordance with one aspect of the present invention, there is provided a 1-phenyl-2-nitroalcohol having the formula I

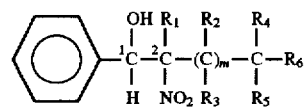

wherein m is an integer from 0 to 3, and each R independently is selected from the group consisting of H, —$CH_3$, and —$CH_2CH_3$.

In the compound of formula I, carbon-1 and carbon-2 are asymmetric, that is, they are chiral centers about which R and S isomers are formed. All other carbons may or may not be asymmetric. The 1-phenyl-2-nitroalcohol, therefore, has a (1R*,2S*) stereoisomer and a (1R*,2R*) stereoisomer. The 1-phenyl-2-nitroalcohol includes greater than about 50% of the (1R*,2S*) stereoisomer. In a preferred embodiment, the nitro-alcohol is 2-nitro-1-phenyl-1-propanol.

In accordance with another aspect of the present invention, there is provided a method for producing a 1-phenyl-2-nitroalcohol of the formula I. The 1-phenyl-2-nitroalcohol produced by this method, likewise, has a (1R*, 2S*) stereoisomer and a (1R*,2R*) stereoisomer. The method comprises the step of reacting benzaldehyde with a nitroalkane of the formula II

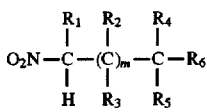

wherein m and R are as defined above. The reaction is carried out in the presence of an amine catalyst. The 1-phenyl-2-nitroalcohol produced by this reaction includes greater than about 50% of the desired (1R*,2S*) stereoisomer.

In a preferred embodiment, a method for producing 2-nitro-1-phenyl-1-propanol is provided. This method comprises reacting benzaldehyde with nitroethane in the presence of an amine catalyst. The 2-nitro-1-phenyl-1-propanol produced by this reaction has a (1R*,2S*) stereoisomer and a (1R*,2R*) stereoisomer. The preferred (1R*,2S*) stereoisomer makes up greater than about 50% of the 2-nitro-1-phenyl-1-propanol. Reduction of this nitro-alcohol produces dl-norephedrine in high yield.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

A surprising new discovery is that the use of an amine catalyst, together with control of the reaction temperature, selectively increases the production of the desired (1R*,2S*) stereoisomer in the production of nitro-alcohols. In particular, reaction of benzaldehyde and nitroethane in the presence of an amine catalyst at low temperature results in production of a 2-nitro-1-phenyl-1-propanol product in which the desired (1R*,2S*)-2-nitro-1-phenyl-1-propanol stereoisomer is present in amounts of up to 80% or more. Production of a phenylpropanolamine product that meets the specifications of USP XXII can thus be carried out simply and economically, without generating unwanted hazardous wastes.

According to an embodiment of the present invention, a 1-phenyl-2-nitroalcohol having the formula I

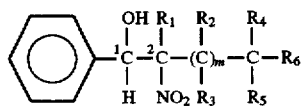

wherein m is an integer from 0 to 3, and each R independently is selected from the group consisting of H, —$CH_3$, and —$CH_2CH_3$ is provided. Carbon-1 and carbon-2 are asymmetric while all other carbons may or may not be asymmetric. The 1-phenyl-2-nitroalcohol has a (1R*,2S*) stereoisomer and a (1R*,2R*) stereoisomer. The 1-phenyl-2-nitroalcohol includes greater than about 50% of the (1R*,2S*) stereoisomer. The 1-phenyl-2-nitroalcohol preferably contains as much as 60% to 80% or higher of the (1R*,2S*) stereoisomer. A specifically preferred nitro-alcohol is 2-nitro-1-phenyl-1-propanol (m=0, each R═H).

According to another embodiment of the present invention, a method for producing 1-phenyl-2-nitroalcohol of the formula I is provided. The 1-phenyl-2-nitroalcohol produced by this method has a (1R*,2S*) and a (1R*,2R*) stereoisomer. The (1R*,2S*) stereoisomer makes up greater than about 50% of the 1-phenyl-2-nitroalcohol, preferably about 60% to 80%. The method comprises the step of reacting benzaldehyde with a nitroalkane having the formula II

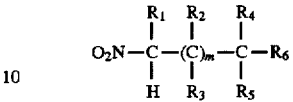

wherein each R is as defined above, in the presence of an amine catalyst.

The nitroalkane of the formula II that is preferred for use in the present invention is nitroethane (m=0, each R═H). Other nitroalkanes, such as nitropropane, nitrobutane, or higher nitroalkane, can also be used.

The nitroalkane is reacted with benzaldehyde to form the 1-phenyl-2-nitroalcohol. Other aromatic aldehydes could be used, for example, a substituted benzaldehyde, to obtain other nitro-alcohol products.

According to an embodiment of the present invention, the reaction is catalyzed by an amine. Amine catalysts have been found to have a high degree of selectivity for producing the desired (1R*,2S*) nitro-alcohol stereoisomer. In a preferred embodiment, the amine catalyst is represented by the formula III $$NR_7R_8R_9 \qquad \text{III}$$

wherein $R_7$, $R_8$ and $R_9$ are each independently an alkyl group, preferably a lower alkyl group such as a $C_{1-3}$ alkyl group, an alkanol group or an alkaryl group such as a benzyl group. $R_7$, $R_8$ and $R_9$ can also each independently be hydrogen. Two of $R_7$, $R_8$ and $R_9$ can also jointly form a 3- to 6- or higher member saturated ring, for example, a piperidine, piperazine, triazine or morpholine ring or like derivative. The amine of formula III should not be sterically hindered (e.g., substituted with t-butyl groups).

Many classes and types of amines have been found useful in the inventive reaction. The amine compound can be mono-, di- or poly-functional with respect to the substituted amine groups. Secondary and tertiary aliphatic amines are preferred, with tertiary aliphatic amines being the most preferred. A preferred tertiary amine is triethylamine, or "TEA" ($R_{7-9}$═—$CH_2CH_3$). Also useful, however, are secondary and tertiary di- and tri-alkanol amines, secondary and tertiary mono-alkyl,di-alkanol amines, cyclic aliphatic amines, secondary and tertiary benzyl amines and morpholine derivatives.

Primary amines, although not as preferred, are also catalytic and have a substantial degree of selectivity for the desired (1R*,2S*) stereoisomer. However, primary amines are capable of forming Schiff base by-products through the action of the primary amine on benzaldehyde. This reduces the overall yield of the nitro-alcohol.

Aniline derivatives, i.e., compounds in which one or more of $R_7$, $R_8$ and $R_9$ are unsubstituted or substituted phenyl groups, are not considered to be within the scope of formula III, and are not favored. Likewise, aromatic compounds such as N-substituted pyridines are not contemplated for use according to the invention. Aromatic amines or aniline derivatives, however, would not be excluded as long as the amine compound has at least one other functional group that is active, for example, it has at least one of the groups listed above as exhibiting catalytic activity.

Amines of several different classes have been evaluated to determine their catalytic activity and selectivity for the production of the desired (1R*,2S*) nitro-alcohol stereoisomer. The results are presented in Table 1.

The data in Table 1 shows that there are many classes and types of amine catalysts that work favorably in the inventive reaction. This table also shows that other amines do not work as favorably. It can be seen, for example, that pyridine exhibits no catalytic activity in the 1-phenyl-2-nitroalcohol reaction. This contradicts the disclosures of the Nagai patents which list pyridine as a catalyst in the benzaldehyde reaction for the production of ephedrine and its homologs.

Another amine, tetramethylammonium hydroxide (a quaternary ammonium hydroxide), is shown to exhibit catalytic activity. However, this catalyst does not selectively produce the desired (1R*,2S*) stereoisomer. Therefore, this is not considered a favored catalyst for use in the reaction of the present invention.

Also included in this table is a control reaction with sodium hydroxide acting as a catalyst. This non-amine showed poor selectivity toward the production of the desired (1R*,2S*) stereoisomer.

nitroalkane used is nitroethane, the optimum temperature range is about −15° C. to 0° C.

Control of the proportions of the reagents used in the reaction are also important in obtaining the desired results. The best results are seen when the ratio of the nitroalkane to benzaldehyde in the reaction mixture is preferably about 1:10 to 10:1, more preferably about 1:1 to 4:1.

The amount of the amine catalyst used in the reaction mixture can also be varied to obtain the most favorable results. The optimum concentration of the amine depends partly upon the type of amine used. Secondary amines exhibit higher activity and can be used in lower concentrations. Tertiary amines are best used in higher concentrations than the secondary amines. The amount of amine catalyst used is measured relative to the amount of the nitroalkane in the reaction mixture. Preferred amounts of a secondary amine are about 0.1% to 250% of the nitroalkane, with 1% to 10% being the most preferred. The tertiary amine pref-

TABLE 1

Evaluation of Amine Catalysts in 1-phenyl-2-nitroalcohol Reaction

| Catalyst | Amine Type | Reactant Mole Ratios | | | Total Conversion %* | (1R*,2S*) in Nitro-alcohol % |
|---|---|---|---|---|---|---|
| | | Benzaldehyde | Nitroethane | Catalyst | | |
| Triethylamine | Tertiary linear aliphatic | 1.00 | 2.91 | 0.97 | 75.3 | 79.3 |
| Diethanolamine | Secondary alkanol | 1.00 | 4.00 | 0.25 | 81.9 | 64.6 |
| Dimethylbenzylamine | Tertiary benzyl | 1.00 | 1.50 | 1.00 | 94.5 | 56.5 |
| Piperidine | Secondary cyclic aliphatic | 1.00 | 4.00 | 0.25 | 89.6 | 59.4 |
| Diethylamine | Secondary linear aliphatic | 1.00 | 4.00 | 0.20 | 99.7 | 68.7 |
| Dimethyl-p-toluidine | Tertiary aniline derivative | 1.00 | 1.50 | 1.00 | N.R. | N.R. |
| Pyridine | Pyridine derivative | 1.00 | 4.00 | 0.25 | N.R. | N.R. |
| 1-phenyl-1,2-propanedione-2-oxime | Oxime | 1.00 | 4.00 | 0.25 | N.R. | N.R. |
| Propylamine | Primary amine | 1.00 | 4.00 | 0.25 | 52.6 | 58.3 |
| Tetramethylammonium hydroxide | Quaternary ammonium hydroxide | 1.00 | 4.00 | 0.25 | 53.6 | 38.8 |
| Benzyltributylammonium chloride | Quaternary ammonium chloride | 1.00 | 4.00 | 0.25 | N.R. | N.R. |
| Sodium hydroxide | Alkali hydroxide (non-amine) | 1.00 | 1.00 | 0.25 | 78.4 | 18.4 |

*Based on limiting reactant
N.R. No reaction

The present invention is characterized in the high fraction of the desired (1R*,2S*) stereoisomer of the 1-phenyl-2-nitroalcohol. By controlling the reaction temperature and the amounts and proportions of the reagents and catalyst as discussed below, a molar fraction of the (1R*,2S*) stereoisomer of at least about 50%, preferably 60% to 80% or higher, can readily be achieved. Neither alkali carbonates or alkali hydroxides used in the prior art processes afford comparable (1R*,2S*) to (1R*,2R*) stereoisomer ratios.

The amine compound, itself, can be employed as a homogeneous catalyst. Alternatively, the amine compound can be incorporated on an insoluble support or an insoluble resin and used as a heterogeneous catalyst.

Control of the reaction temperature and of the proportions of the reagents and the amine catalyst are important in achieving the desired ratio of the (1R*,2S*) to the (1R*,2R*) stereoisomer according to the invention. With respect to reaction temperature, the reaction can be carried out at about −15° C. to 30° C. The reaction preferably is carried out at low temperature, desirably at about −15° C. to 0° C. The reaction can be carried out at higher temperatures, such as room temperature, with lower yields. Even at higher temperatures, however, the inventive reaction achieves overall yields and (1R*,2S*) to (1R*,2R*) stereoisomeric ratios unexpectedly higher than are achieved according to the present benzaldehyde process.

The optimum temperature for conducting the reaction also depends on the particular nitroalkane used. When the erably is employed in an amount from about 10 mol % to 250 mol % of the nitroalkane employed, more preferably about 50 mol % to 150 mol %. By adjusting the temperature, the reactant ratio and the amine concentration, the reaction can be regulated so as to selectively encourage production of the desired (1R*,2S*) nitro-alcohol stereoisomer.

The inventive reaction is reversible, and if allowed to proceed for extended periods or at higher temperatures reaches an equilibrium (1R*,2S*) to (1R*,2R*) stereoisomeric ratio that is approximately the same undesirable ratio produced by the methods of the prior art. Neutralization or removal of the catalyst is needed to quench the reaction or "freeze" the isomer ratio at a more favorable ratio that exists at the time of the quench. Neutralization of the catalyst can be accomplished by lowering the pH.

The reaction can be conducted so that either the nitroalkane or benzaldehyde is the limiting reactant. Typically, the reaction is conducted with an excess of the nitroalkane. This causes benzaldehyde to be the limiting reagent.

Another aspect of conducting the reaction in an excess of the nitroalkane is that no additional reaction solvent need be used. The reaction could, however, also be conducted in the presence of an inert reaction solvent. Common solvents, such as aliphatic alcohols, aliphatic and aromatic hydrocarbons, and others could be utilized. Solvents that are reactive with the nitroalkane, however, would not be useful.

Ketone based solvents, for example, which react with the nitroalkane are disfavored. Any of the above mentioned solvents might also contain various amounts of water.

A particular preferred embodiment of the present invention is an improved method for producing 2-nitro-1-phenyl-1-propanol. This is achieved by reacting benzaldehyde with nitroethane in the presence of an amine catalyst. The 2-nitro-1-phenyl-1-propanol produced contains at least about 50% of the (1R*,2S*) stereoisomer, but can be as high as 60% to 80% or higher when carried out at low temperature. In particular, a reaction temperature of −15° C. to 0° C. is preferred. A favored amine catalyst for this reaction is a tertiary amine, preferably triethylamine.

The production of dl-norephedrine and its homologs can be achieved according to another embodiment of the present invention. First, a 1-phenyl-2-nitroalcohol is formed as described above, by the method of reacting benzaldehyde with a nitroalkane in the presence of an amine catalyst. The 1-phenyl-2-nitroalcohol formed by this reaction is then reduced to form a compound of the formula IV.

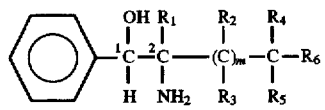

IV

Dl-norephedrine (m=0, each R=H) can be produced in this manner by reacting benzaldehyde with nitroethane in the presence of an amine catalyst according to the present invention to produce 2-nitro-1-phenyl-1-propanol, and reducing the 2-nitro-1-phenyl-1-propanol.

Reduction of an organic molecule usually corresponds to increasing the hydrogen content or decreasing the oxygen content of a molecule. The reduction of the 1-phenyl-2-nitroalcohol in an embodiment of the present reaction is achieved by any method of hydrogenation known in the art, preferably by catalytic hydrogenation.

The invention is further illustrated by the following non-limiting examples.

EXAMPLE 1

Nitroethane (10.2 g., 0.132 mole) was mixed with triethylamine (17.1 g., 0.169 mole), cooled to a temperature of −8° C. and benzaldehyde (5.1 g., 0.047 mole) added. After 2.7 hours at −10° C., the mixture was neutralized. HPLC analysis showed a conversion of 8.25 g. (96.9%) of total 2-nitro-1-phenyl-1-propanol. 6.40 g of the 2-nitro-1-phenyl-1-propanol was the (1R*,2S*)-stereoisomer (77.6%).

EXAMPLE 2

Nitroethane (15.6 g., 0.208 mole) was mixed with triethylamine (17.1 g., 0.169 mole), cooled to a temperature of −8° C. and benzaldehyde (5.02 g., 0.047 mole) added. After 2.25 hour reaction time, at −10° C., the mixture was neutralized. HPLC analysis showed a conversion of 8.30 g (96.9%) of total 2-nitro-1-phenyl-1-propanol with a (1R*,2S*)-stereoisomer content of 6.11 g. (74.1%).

CONTROL I (Method of Vanderbilt and Hass)

Benzaldehyde (13.28 g., 0.125 mole), nitroethane (9.41 g., 0.125 mole), 47.5 ml of SDA-2B alcohol and 3.5 ml of water were mixed and 1 ml of sodium hydroxide solution (50%) was added with cooling. After a 75 hour reaction time, at room temperature, the sodium hydroxide was neutralized. HPLC analysis showed a conversion of 16.2 g. (71.6%) of total 2-nitro-1-phenyl-1-propanol with an amount of (1R*,2S*)-stereoisomer of 5.5 g. (33.9%).

CONTROL II (Modified Method of Vanderbilt and Hass)

Benzaldehyde (13.29 g., 0.125 mole), nitroethane (9.39 g., 0.125 mole), 47.5 ml of SDA-2B alcohol and 3.5 ml of water were mixed and cooled to −10° C. To the cooled mixture was added 1.0 ml of sodium hydroxide solution (50%) and the reaction was allowed to proceed for 75 hours, at −10° C., after which time the sodium hydroxide was neutralized. HPLC analysis showed a conversion of 19.3 g. (85.4%) of total 2-nitro-1-phenyl-1-propanol with a (1R*,2S*)-isomer content of 6.4 g. (33.1%).

CONTROL III (Method of Kamlet)

Benzaldehyde (106.1 g., 1.0 mole) was agitated with sodium bisulfite (100.6 g., 1.06 mole) in 500 ml of water for 30 minutes. Separately, nitroethane (82.5 g., 1.10 mole) was dissolved, with cooling, in a solution made from 50% sodium hydroxide (90.9 g., 1.13 mole) and 155 ml of water. This mixture was added, over a period of 15 minutes, at 25° C., with vigorous agitation to the addition product of benzaldehyde and sodium bisulfite. After stirring overnight, the lower layer was discarded. HPLC analysis of the upper layer showed a conversion of 125.4 g. (69.3%) of total 2-nitro-1-phenyl-1-propanol with a (1R*,2S*)-isomer content of 43.9 g. (35.1%).

EXAMPLES 3–17

In the same manner as Examples 1 and 2, a nitroalkane, benzaldehyde and an amine catalyst were mixed in various ratios and proportions and allowed to react as indicated in Table 2.

TABLE 2

Preparation of 1-phenyl-1-nitroalcohols

| | Conditions | | Reactants | | Reactant Mole Ratios | | | Total | (1R*,2S*) in |
|---|---|---|---|---|---|---|---|---|---|
| Example | Min | Deg C. | Nitroalkane | Catalyst | Nitroalkane | Benzaldehyde | Catalyst | Conversion %* | Nitro-alcohol % |
| 3 | 1365 | −10 | 1-nitropropane | Triethylamine | 4.00 | 1.00 | 1.00 | 88.4 | 58.5 |
| 4 | 3075 | −12 | Nitroethane | Dimethylbenzylamine | 1.50 | 1.00 | 1.00 | 94.5 | 56.5 |
| 5 | 42 | −5 | Nitroethane | Propylamine | 4.00 | 1.00 | 0.25 | 52.6 | 58.3 |
| 6 | 55 | −13 | Nitroethane | Piperidine | 4.00 | 1.00 | 0.25 | 89.6 | 59.4 |
| 7 | 370 | −8 | Nitroethane | Triethylamine | 1.00 | 2.12 | 2.59 | 100.8 | 63.0 |
| 8 | 220 | −10 | Nitroethane | Diethanolamine | 4.00 | 1.00 | 0.25 | 81.9 | 64.6 |
| 9 | 205 | −10 | Nitroethane | Triethylamine | 1.00 | 2.10 | 0.16 | 83.6 | 66.0 |
| 10 | 130 | −10 | Nitroethane | Triethylamine | 1.00 | 3.60 | 0.31 | 91.9 | 67.7 |

TABLE 2-continued

Preparation of 1-phenyl-1-nitroalcohols

| | Conditions | | Reactants | | Reactant Mole Ratios | | | Total | (1R*,2S*) in |
|---|---|---|---|---|---|---|---|---|---|
| Example | Min | Deg C. | Nitroalkane | Catalyst | Nitroalkane | Benzaldehyde | Catalyst | Conversion %[a] | Nitro-alcohol % |
| 11 | 1120 | −13 | Nitroethane | Triethylamine | 1.00 | 1.03 | 2.49 | 91.0 | 68.1 |
| 12 | 45 | −10 | Nitroethane | Diethylamine | 4.00 | 1.00 | 0.20 | 99.7 | 68.5 |
| 13 | 60 | −5 | Nitroethane | Triethylamine | 1.00 | 3.63 | 0.99 | 91.3 | 69.2 |
| 14 | 305 | −8 | Nitroethane | Triethylamine | 2.66 | 1.00 | 4.94 | 95.2 | 73.0 |
| 15 | 543 | −10 | Nitroethane | Triethylamine | 1.00 | 6.94 | 0.29 | 77.1 | 73.3 |
| 16 | 75 | −13 | Nitroethane | Triethylamine | 1.00 | 2.09 | 0.46 | 81.4 | 74.9 |
| 17 | 155 | −10 | Nitroethane | Triethylamine | 2.91 | 1.00 | 0.97 | 75.3 | 79.3 |

[a]Based on limiting reactant

The data presented in Table 2 demonstrates that a nitro-alcohol with a high yield of the desired (1R*,2S*) stereoisomer can be produced by the method of the present invention. By use of an amine catalyst and careful control of the reaction conditions, including the reaction temperature and reagent ratios, nitro-alcohols having a high yield of the (1R*,2S*) stereoisomer are produced. Upon reduction, these compounds form dl-norephedrine and its homologs.

A method for producing high yields of phenylpropanolamine meeting the standards of the USP XXII, without the accompanying generation of hazardous waste, is thus provided.

What is claimed is:

1. A method of producing a 1-phenyl-2-nitroalcohol of the formula

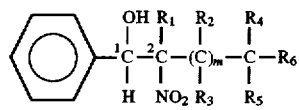

wherein m is an integer from 0 to 3, and each R independently is selected from the group consisting of H, —CH$_3$ and —CH$_2$CH$_3$, such that carbon-1 and carbon-2 are asymmetric, said 1-phenyl-2-nitroalcohol having a (1R*,2S*) stereoisomer and a (1R*,2R*) stereoisomer, said method comprising the step of reacting a sufficient amount of benzaldehyde with a sufficient amount of nitroalkane having the formula II

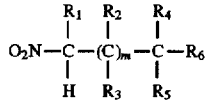

wherein m is as defined above, and each R is as defined above, in the presence of a catalyst, which consists essentially of an amine catalyst, at a temperature in a range of about −15° C. to about 30° C. such that the yield of said 1-phenyl-2-nitroalcohol is greater than about 50%, and wherein said 1-phenyl-2-nitroalcohol includes greater than about 50% of said (1R*,2S*) stereoisomer.

2. The method according to claim 1 wherein said 1-phenyl-2-nitroalcohol includes about 60% to 80% of said (1R*,2S*) stereoisomer.

3. The method according to claim 1 wherein said nitroalkane is nitroethane.

4. The method according to claim 1 wherein said amine has the formula III

NR$_7$R$_8$R$_9$    III wherein

R$_7$, R$_8$ and R$_9$ independently are selected from the group consisting of H, alkyl, benzyl, alkaryl and alkanol, or in which two among R$_7$, R$_8$ and R$_9$ jointly form a 3- to 6-member saturated ring.

5. The method according to claim 4 wherein said amine is a secondary amine.

6. The method according to claim 4 wherein said amine is a tertiary amine.

7. The method according to claim 6 wherein said tertiary amine is triethylamine.

8. The method according to claim 1, in which the reaction is maintained at a temperature of from −15° C. to 0° C.

9. The method according to claim 1 wherein said nitroalkane and said benzaldehyde are combined in a reagent ratio of from 1:10 to 10:1.

10. The method according to claim 9 wherein said nitroethane and said benzaldehyde are combined in a reagent ratio of from 1:1 to 4:1.

11. The method according to claim 1 wherein the reaction is conducted with an excess of nitroalkane.

12. The method according to claim 5 in which said secondary amine is present in an amount from 0.1 mol % to 250 mol % of said nitroalkane.

13. The method according to claim 12 in which said secondary amine is present in an amount from 1 mol % to 10 mol % of said nitroalkane.

14. The method according to claim 6 wherein said tertiary amine is present in an amount from 10 mol % to 250 mol % of said nitroalkane.

15. The method according to claim 14 wherein said tertiary amine is present in an amount from 50 mol % to 150 mol % of said nitroalkane.

16. A method of producing 2-nitro-1-phenyl-1-propanol having a (1R*,2S*) stereoisomer and a (1R*, 2R*) stereoisomer consisting essentially of the step of reacting benzaldehyde with nitroethane in the presence of an amine catalyst, wherein the 2-nitro-1-phenyl-1-propanol includes at least about 50% of said (1R*,2S*) stereoisomer.

17. The method according to claim 16 wherein said 2-nitro-1-phenyl-1-propanol includes about 60% to 80% of said (1R*,2S*) stereoisomer.

18. The method according to claim 16 in which said amine catalyst is a tertiary amine.

19. The method according to claim 18 wherein said tertiary amine is triethylamine.

20. The method according to claim 16 in which the reaction is maintained at a temperature of from −15° C. to 0° C.

* * * * *